US 6,699,511 B2

(12) United States Patent
Macias Camero et al.

(10) Patent No.: US 6,699,511 B2
(45) Date of Patent: Mar. 2, 2004

(54) METHOD OF OBTAINING PINITOL FROM CAROB EXTRACTS

(75) Inventors: Blas Macias Camero, Valencia (ES); Carlos Sanjuan Merino, Valencia (ES)

(73) Assignee: Compania General del Algarrobo de Espana S.A. (ES)

( * ) Notice: Subject to any disclaimer, the term of this patent is extended or adjusted under 35 U.S.C. 154(b) by 0 days.

(21) Appl. No.: 09/924,830

(22) Filed: Aug. 8, 2001

(65) Prior Publication Data

US 2003/0040609 A1 Feb. 27, 2003

(30) Foreign Application Priority Data

Mar. 16, 2001 (ES) .............................. 0100617

(51) Int. Cl.⁷ ..................... A01N 65/00; A61K 35/78; C12N 5/00; C12N 5/02
(52) U.S. Cl. ....................... 424/725; 435/410
(58) Field of Search .................. 435/410, 254.7, 435/240.4, FOR 100, FOR 114; 424/725, 58, 74, 93.7; 536/123.1, 124, 1.11

(56) References Cited

U.S. PATENT DOCUMENTS

| 5,428,066 A | * 6/1995 | Larner et al. ................ 514/738 |
| 5,482,631 A | 1/1996 | Saska et al. ................ 210/635 |

FOREIGN PATENT DOCUMENTS

| EP | 0617133 | 9/1994 |
| ES | 2060544 | 11/1994 |
| WO | 96/29063 | * 9/1996 |

* cited by examiner

*Primary Examiner*—David M. Naff
*Assistant Examiner*—Deborah K Ware
(74) *Attorney, Agent, or Firm*—Ostrolenk, Faber, Gerb & Soffen, LLP

(57) ABSTRACT

Pinitol is obtained from carob extracts by inversion of saccharose contained in the extracts to fructose and glucose to obtain a syrup, then subjecting the syrup to chromatographic separation by means of ion-exchange resins to obtain a solution of pinitol in water, and separating of the pinitol from said solution. The solution of pinitol in water preferably contains 90% or greater pinitol content. The ion-exchange resins may be strong cationic or strong anionic exchange resins.

9 Claims, 1 Drawing Sheet

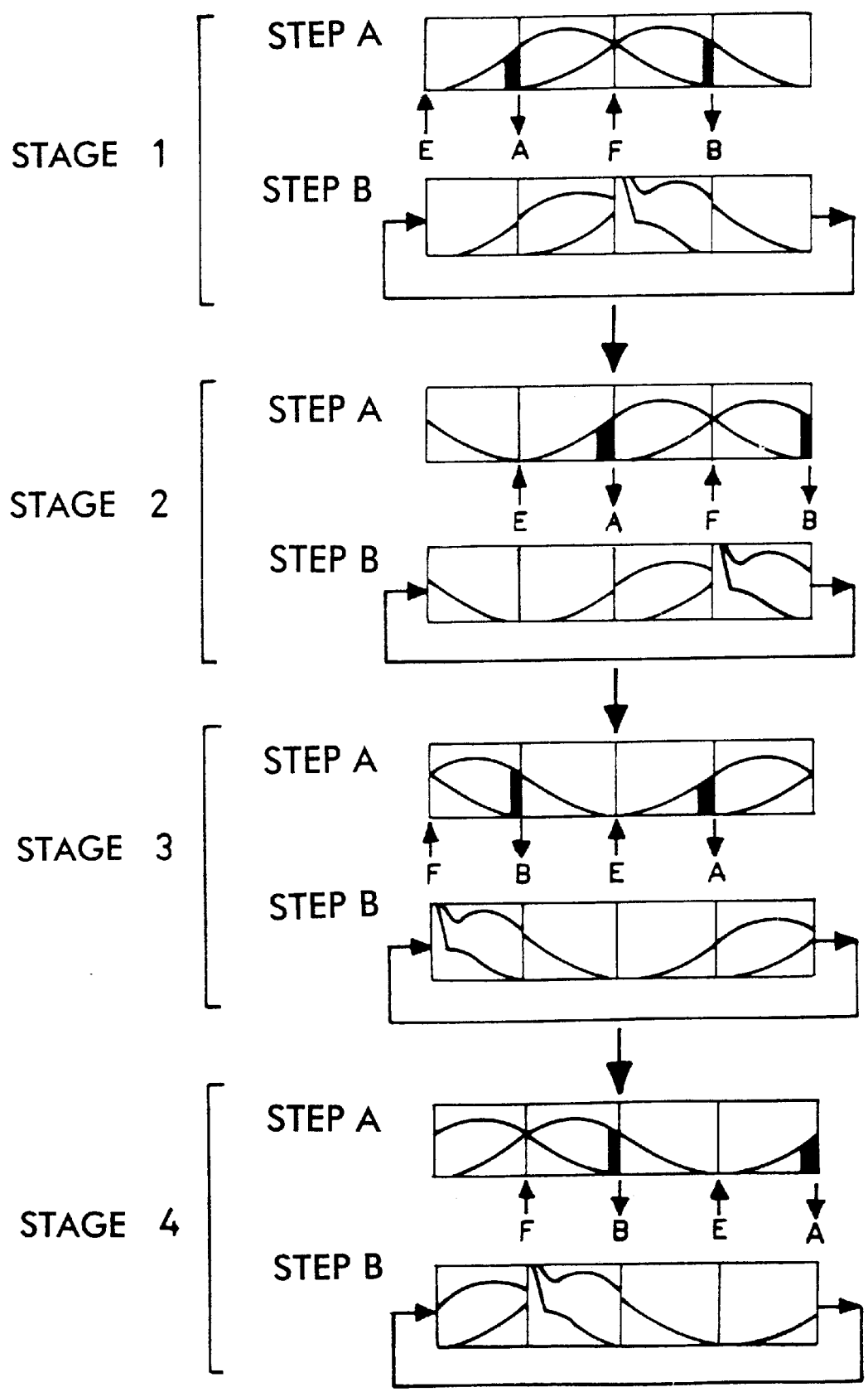

METHOD OF OBTAINING PINITOL FROM CAROB EXTRACTS

BACKGROUND OF THE INVENTION

This invention relates to a method of obtaining pinitol from carob extracts using chromatographic techniques on ion-exchange resins.

Pinitol is a cyclitol corresponding to the methylated form of D-chiro-inositol and more concretely it is 3-O-methyl-1,2,4 cis-3,5,6 transhexahydroxycyclohexanol.

The name pinitol derives from "pine", as it had been isolated from this tree. (Ballou C. E., Anderson A. B., J. Am. Chem. Soc. 75, 648–670 (1953)). It also occurs widely in other plants such as: soya (Phillips D. V., Smith A. E., J. Agric. Food Chem. 30, 456–466 (1982)), in leaves of *Bougainvillea spectabilis* (Narayana C. R., Joshi D. D., Mujumdar A. M., Dhekne V. V., Current Science 56, 130–141 (1987)), in leaves of *Gliricidia sepium* (Calle J., Rivera A., Joseph-Nathan P., Planta Med. 53, (3), 303 (1987)), etc.

Pinitol can also be obtained by chemical synthesis, but until now the process has been very expensive.

Pinitol is a normal component of the human diet. It is present in soya at about 1% of dry weight (Ostlund et al., U.S. Pat. No. 5,550,166). In some Asian countries, where consumption of soya is very widespread, it is calculated that the consumption of pinitol, via soya, is greater than 5 mg/kg/day.

In PCT WO 00/71111 A1 of Humanectics Corporation, it is claimed that pinitol enhances the function of muscle tissue, increases the formation of glycogen in muscle and stimulates the transport of glucose within muscle tissue.

The use of pinitol for the treatment of disorders associated with resistance to insulin is claimed in PCT WO 96/29063 of Washington University. Therefore, pinitol can be used for treatments connected with diabetes mellitus and its chronic complications; obesity, hyperlipidemias, dyslipidemias, atherosclerosis, hypertension, cardiovascular disorders, AIDS, cancer, malnutrition, stress, lupus and other autoimmune disorders, endocrin disorders and complications arising from athletic activity or from inactivity.

Pinitol is used at a dose from 0.1 mg to 1.0 g per day per kg of weight. It can be administered orally, parenterally or intravenously.

The aforementioned document PCT WO 96/29063 also describes a method of obtaining pinitol from soluble fractions of soya, in which said fractions are first deproteinized and treated with active carbon before undergoing column chromatography.

According to this known method, after deproteinization and treatment with active carbon, the material is deionized by passing it over ion-exchange resins and then the sugars are separated by means of anionic resins. The resulting fraction, rich in cyclitols, is employed for pharmacological tests.

On the other hand, U.S. Pat. No. 5,482,631 describes a method of separating inositols and sugars from an aqueous phase of sugar cane molasses, beet, almonds and soya, which comprises passing said aqueous phase over a strong anionic exchange resin of the hydroxide form. The process is preferably carried out in a simulated moving-bed chromatographic system, details of which will be given later.

As is clear from the state of the art noted above, production of pinitol basically employs ion-exchange techniques using strong anionic exchange resins of the OH form, and starting from materials such as soya, sugar cane molasses, beet and almonds.

In addition to WO 96/29063 and U.S. Pat. No. 5,482,631, the use of strong anionic resins of the OH form for the separation of carbohydrates is mentioned in Roseman et al., Arch. Biochem. Biophys. 36, 232, (1952); and Phillips et al., J. Agric. Food Chem. 30, 456–458 (1982).

The use of resins of this type has the advantage of good separation of the cyclitols from the carbohydrates. On the other hand, it has serious drawbacks. Firstly, there is decomposition of the sugars in an alkaline medium and, secondly, the adsorption often has a high degree of irreversibility, all of which gives rise to difficulties for the regeneration of these resins and hence a very short useful life and very high costs.

Accordingly, it is more interesting to use strong cationic resins (Na, K, Li, Ca, etc.), which are more stable and for which the adsorption effects are clearly reversible.

Thus, patent ES 2060544 describes a method for obtaining a syrup consisting of the natural sugars of the carob, which comprises extracting the sugars from carob pulp and submitting the juice thus obtained to chromatographic separation to separate the sugars from the non-sugars.

Before commenting on the method of patent ES 2060544, it should be pointed out that carob, used as the starting material in said method, is the fruit of the carob tree (*Ceratonia siliqua*), a slow-growing tree of medium size, evergreen, originating from the Mediterranean area. It belongs to the leguminosae and is the only member of the genus ceratonia. It grows in dry environments. Its pods are the carob beans. The carob tree is encountered abundantly throughout the Mediterranean basin. Spain is the largest producer of carob, with almost 50% of the total.

The use of carob as a human and/or animal food product has been known since antiquity. It has a long history of application as foodstuff and as a pharmaceutical product.

It has also found wide application as a cocoa substitute. Relative to cocoa, it has the advantage that it is not allergenic, and does not produce the effect of addiction of caffeine and theobromine. It contains less fat and more sugars.

The yellowish-white powder of the carob seed (GARROFIN) is used as an additive in the food industry (ice creams, jams, etc.).

Carobs are characterized as being rich in sugars. The average amount of saccharose, glucose and fructose is in the range 40–50% based on dry matter of the carob.

These comments concerning carob having been made, the method of patent ES 2060544 comprises a series of stages for extracting the sugars from the carob pulp, which include, in summarized form:

cleaning of the carob; cutting into pieces; classification; extraction with water; pressing of the husks; prefiltration; decalcification; fine filtration; evaporation and preliminary concentration; chromatographic separation of sugars and non-sugars; demineralization and decolorizing by resins; and evaporation and final concentration.

Concretely, in relation to the stage of chromatographic separation of sugars and non-sugars, patent ES 2060544 employs a strong cationic resin, based on weakly crosslinked polystyrene, whose active sulfonic groups are charged with a monovalent or divalent cation, thus arriving at a carob syrup with the following composition:

| Saccharose | 55–75% |
|---|---|
| Fructose | 7–15% |
| Glucose | 7–16% |
| Other sugars | 0.5–3% |
| Cyclitols | 4–14% |
| Organic and inorg. impurities | 0.5–2% |

The syrup thus obtained consists of the natural sugars of the carob and is free of the adverse characteristics of color, odor and flavor of the natural extract of carob.

According to Saura Calixto F (An. Bromatol. 39 (1), 81–93 (1987)), analysis of carob pulp by HPLC and gas chromatography gives the result:

| Saccharose | 69.9–70.2% |
|---|---|
| Pinitol | 10.2–11.0% |
| Glucose | 9.6–9.9% |
| Fructose | 7.4–8.2% |
| Myo-inositol | 1.1–1.4% |
| Xylose | 0.6% |

In view of these data, it would be desirable to have a method of obtaining pinitol from carob extracts.

In this connection, a method is known for the production of pinitol by fermentation of carob extracts. Thus, Baumgartner et al. (J. Agric. Food Chem., 34, 827–829 (1986)) ferment carob extracts with *Saccharomyces bayanus* at 30° C. for seven days. Pinitol is isolated and identified from the fermented product. Analyses by TLC, gas chromatography and GC-MS made it possible to determine the composition of the fermented carob extract, which was:

| Pinitol | 5–7.5% |
|---|---|
| Myo-inositol | 0.5–1% |
| Chiroinositol | 0.1% |
| Ononitol | Traces |
| Segnoyitol | Traces |
| Bornesitol | Traces |

It has now been demonstrated that, starting from the carob syrup obtained according to patent ES 2060544, it is possible to separate and recover pinitol by means of ion-exchange resins, both strong anionic resins and strong cationic resins.

SUMMARY OF THE INVENTION

Accordingly, the aim of the present invention is to provide a method of obtaining pinitol starting from carob extracts that have the composition:

| Saccharose | 55–75% |
|---|---|
| Fructose | 7–15% |
| Glucose | 7–16% |
| Other sugars | 0.5–3% |
| Cyclitols | 4–14% |
| Org. and inorg. impurities | 0.5–2% | in which the percentages are expressed in weight of dry matter, distinguished by the fact that, once the saccharose contained in the extract has been inverted to fructose and glucose, the resulting syrup is submitted to chromatographic separation of the pinitol by means of ion-exchange resins, strong anionic or strong cationic, to obtain a solution of pinitol in water, after which the pinitol is separated from said solution. Preferably, the pinitol is separated from said solution by concentration and addition of an organic solvent or by atomization and freeze-drying.

BRIEF DESCRIPTION OF THE FIGURE

The sole FIGURE schematically illustrates the technique of continuous simulated moving-bed chromatographic separation.

DESCRIPTION OF THE INVENTION

In accordance with the invention, the carob extract in which the saccharose has been inverted basically contains glucose, fructose, pinitol and non-sugars. It is possible to separate the pinitol from this syrup by the use of ion-exchange resins, strong anionic or strong cationic.

As has been pointed out already, the use of strong cationic resins has the advantage that they are much more economical and stable, and the adsorption is reversible.

As non-exclusive examples of strong cationic resins, DIAION UBK 530® (Na) and UBK 555® (Ca) (Resindion S.r.l., Milan) are preferably employed in the present invention.

The strong cationic resins can be used salified in the form of Na, K, Li, Ca, etc. The sodium or potassium form is the commonest. Chromatographic columns of various sizes can be used. Elution is always effected with demineralized water, and regeneration of the resin is not necessary because after washing with demineralized water it is ready for reloading. It is possible to work at any temperature, from close to zero degrees Celsius to close to the boiling point. According to the invention, it is preferable to work at about 60° C., to avoid microbiological contamination. The components of the carob extract are separated in columns of cationic resin UBK 530® with a diameter of 2 cm and a height of 100 cm, at a temperature of 60° C. The non-sugars run quickly, followed by the pinitol and finally the glucose and the fructose. The $t_R$ values are: 9.9 min for pinitol, 11.5 min for glucose and 13.2 min for fructose.

The retention times of the individual substances are not sufficiently different for there to be complete separation of each substance, and therefore there is some overlapping of the peaks.

As already mentioned, an important advantage is that elution is carried out simply with demineralized water, leaving the column, immediately after elution, ready for reuse without the need for any type of regeneration. These characteristics are typical when employing the technique known as ISMB® (IMPROVED SIMULATED MOVING BED), which makes it possible to separate mixtures made up of overlapping "peaks", with continuous operation, in addition carrying out partial recirculation. This technique will be explained later.

The carob extract that is submitted to chromatographic separation according to the invention for production of pinitol is obtained by the following stages of operation:

Preparation of the Carob Syrup

The clean, dry carob is ground and then the pulp is separated from the seed. The carob pulp thus obtained is submitted to extraction with water between 10 and 70° C., more often between 15 and 30° C. and at slightly acid pH, but concretely between 4.6 and 5.4. Contact time is between 1 and 3 hours. An extract is obtained between 30 and 50° Brix.

The moist residual pulp is pressed to remove most of the retained water.

The raw juice thus obtained is filtered, then the filtrate is passed through a strong cationic resin (Na) so that the greater part of the calcium and magnesium ions contained therein is retained. Next, the juice is submitted to microfiltration (or ultrafiltration) to clear it completely of suspended solids and microorganisms.

Finally the syrup obtained is concentrated to approx. 60° Brix.

Inversion of the Saccharose Contained in the Syrup

This can be carried out either by an enzymatic method or by an acid method using cationic resins (H), such as RPI resin (Resindion S.r.l., Milan).

Demineralization and Decolorizing

Syrup at a concentration of 20–30° Brix can be demineralized and decolorized by passing it successively through strong cationic resins (H) and then through strong anionic resins (OH). Generally, according to the invention, the resins EXA-140®, RPS®, RAP3®, PAP 1®, DCA®, RAM 1® (Resindion S.r.l., Milan) are used, though any similar resin can be used. The specific conductivity after demineralization is less than 10 $\mu\Omega$ and the color is less than 25 Icumsa at 420 nm.

As already pointed out, the chromatographic separation of pinitol using strong cationic exchange resins is carried out preferably using the ISMB® technique (continuous chromatographic separation).

Starting from the 1970s, a number of chromatographic methods permitting continuous operation have been under development. These give pure products, although the chromatographic separations are not clear. In our opinion, the method that best solves the numerous problems involved in separations of this type is the method developed by MITSUBISHI KASEI CORPORATION and known as "IMPROVED SIMULATED MOVING BED" (ISMB®). More or less inspired by this, others have been developed that could also be applied to the carob extracts used as starting material in the method of the present invention.

The characteristics of ISMB® are:

To reduce the costs of capital investment and reduce the volume of separating resin employed, four columns are used, connected together in series.

Operation is such that dynamic equilibrium is maintained within each column, permitting a constant distribution of the concentration profiles of the components of the mixture.

The use of beds of resins with very narrow ranges of size distribution helps to improve the quality of separation.

It is absolutely essential to achieve good systems for distribution and collection which ensure a uniform flow rate over the whole section along the length of the column. Uniform flow rates are critical for achieving good separations especially when the columns are of large diameter. MITSUBISHI has achieved it in columns of up to 5 meters in diameter.

The operation of the ISMB® is shown schematically in the diagram. As already mentioned, the number of columns/chambers is four, as illustrated in each step of the FIGURE.

In stage 1, Step 1A, the four columns are equilibrated and the distribution of the mixture of substances R and P is as indicated by the curves of the concentration profile. At this moment, fraction R is being removed at A, and fraction P is removed at B. The initial problematic mixture is fed at E, and the water eluent is fed at F.

The concentration profile moves toward the right, so that after a certain time during which liquids enter and leave, the concentration profile has been altered until it is as shown in Step 1B.

In Step 1B, recirculation begins with all the feeds and discharges, that is, E, A, B and F stopped.

The concentration profile continues to be shifted toward the right, developing until it reaches Step 2A. At this moment there is change of positions of mixture feed (E), collection of fraction R (A), collection of fraction P (B) and water feed (F).

When the concentration profile reaches the position of Step 2B, all additions and collections are shut off and recirculation starts again.

Then Step 3A is reached, continuing until Step 4B is completed.

Starting from Step 4B, the distribution corresponding to Step 1A is reconstituted and the cycle begins again.

Mitsubishi has developed the corresponding equipment, as well as methods enabling all the operations to be programmed in a computer and to be carried out automatically.

The method of the invention will be illustrated below, with the following examples, which should not be regarded as limiting the invention.

EXAMPLE 1

Chromatographic Separation (ISMB®) of Pinitol and Reducing Sugars

The carob syrup obtained as indicated previously, but with the saccharose inverted and with a concentration of approx. 60° Brix, is used as the feed for an ISMB® plant characterized by the following operating parameters:

| Resin | UBK 530 ® |
|---|---|
| Volume of resin | 4 m³ |
| Feed rate | 0.038 L/h |
| W/F | 3.750 v/v |
| P/R | 2.166 v/v |
| Temperature | 65.0° C. |
| Feed capacity | 2.07 T/D |
| Capacity of pinitol fraction | 0.36 T/D |

The results of operation by ISMB® are presented in the following table:

| | FEEDS | | | EXTRACTS | | | | RECOVERY |
|---|---|---|---|---|---|---|---|---|
| | FEED | | WATER | R.S. FRACTION | | PINITOL FRACTION | | R.S. FRAC |
| | TON/DAY | % W | TON/DAY | TON/DAY | % W | TON/DAY | % W | % W |
| FRUCTOSE | 0.74 | 35.60 | — | 0.73 | 42.71 | 0.01 | 2.42 | 98.80 |
| GLUCOSE | 0.76 | 36.80 | — | 0.75 | 44.11 | 0.01 | 2.71 | 98.70 |
| PINITOL | 0.35 | 17.00 | — | 0.17 | 9.78 | 0.18 | 50.61 | 47.40 |

-continued

| | FEEDS | | | EXTRACTS | | | | RECOVERY |
|---|---|---|---|---|---|---|---|---|
| | FEED | | WATER | R.S. FRACTION | | PINITOL FRACTION | | R.S. FRAC |
| | TON/DAY | % W | TON/DAY | TON/DAY | % W | TON/DAY | % W | % W |
| NON-SUGARS | 0.22 | 10.60 | — | 0.06 | 3.40 | 0.16 44.20 26.40 | | |
| Dry solids | 4.07 | (100.0) | | 1.70 | (100) | 0.36 | (100.0) | 82.35 |
| Water | 2.07 | | 12.66 | 9.91 | | 4.81 | | |
| Total | 4.13 | | 12.66 | 11.62 | | 5.18 | | |
| % w solids | | 50.00 | | | 14.65 | | 7.04 | |
| Flow rate m3/h | 0.143 | | 0.538 | 0.466 | | 0.215 | | |
| Density ton/m3 | 1.201 | | 0.981 | 1.039 | | 1.003 | | |

The pinitol fraction thus obtained contains 44.2% of salts, therefore it has to be demineralized and decolorized, as indicated previously. Then, the composition of the extract is:

| | |
|---|---|
| Pinitol | 90% |
| Glucose | 5% |
| Fructose | 5% |

This fraction is concentrated and crystallized with the addition of ethanol. The pinitol obtained possesses the following characteristics:

| | |
|---|---|
| Purity HPLC | 95% |
| Specific rotatory power | (+) 64 |
| Moisture content | 2% |

The structure of the pinitol was confirmed by NMR and $^{13}$C spectra.

EXAMPLE 2

Isolation of Pinitol by Means of Strong Anionic Resins.

70 ml of a carob extract, inverted, demineralized and decolorized, with 25° Bx and a composition based on dry weight:

| | |
|---|---|
| Pinitol | 35% |
| Glucose | 27% |
| Fructose | 37% |
| Non-sugars | 0.4% | were passed through 250 ml of resin SA 11A (OH), contained in a column with a diameter of 2 cm and a height of 100 cm, at a rate of 10 ml/m and elution was continued with demineralized water. The entire operation was carried out at 6° C. Fractions that give positive ° Brix are collected.

The fractions with positive ° Brix are mixed and concentrated. The concentrate is crystallized with ethanol. The filtered, dry product obtained gave a weight of 2.5 g of pinitol with the following characteristics:

| | |
|---|---|
| Purity HPLC | 91% |
| Specific rotatory power | (+) 63 |
| Moisture content | 2.5% |

EXAMPLE 3

This example starts from the carob syrup that the Compañía General del Algarrobo obtains industrially by carob extraction according to the method described in patent ES 2060544. Said syrup, once inverted, has the following composition:

| | |
|---|---|
| Non-sugars | 0.76% |
| Pinitol | 15.73% |
| Glucose | 45.99% |
| Fructose | 37.52% |

(% expressed on the basis of dry weight)

The aforementioned syrup is used as feed for an ISMB pilot plant operating with the following parameters:

| | |
|---|---|
| Resin | UBK 530 |
| Resin Vol. | 1400 ml |
| Feed (D.S.) | 557 g/D |
| P-frac (D.S.) | 463 g/D |
| R-frac (D.S.) | 83 g/D |
| Load | 0.022 l/h |
| W/F | 5.000 v/v |
| P/R | 1.842 v/v |

The results of chromatographic separation are presented in the following table:

|  | Feed component | | Eluent | P-fraction | | R-fraction | | Recovery-R |
| --- | --- | --- | --- | --- | --- | --- | --- | --- |
|  | g/D | % | g/D | g/D | % | g/D | % | % |
| Non-sugars | 4.231 | 0.76 |  | 1.528 | 0.33 | 2.618 | 3.14 | 63.14 |
| PINITOL | 87.566 | 15.73 |  | 6.670 | 1.44 | 78.901 | 94.64 | 92.21 |
| Glucose | 256.017 | 45.99 |  | 252.289 | 54.47 | 1.701 | 2.04 | 0.67 |
| Fructose | 208.866 | 37.52 |  | 202.637 | 43.75 | 0.150 | 0.18 | 0.07 |
| Total D.S. | 556.678 | 100 |  | 163.171 | 100 | 83.370 | 100 | 16.25 |
| Eluent (Water) | 368.037 |  | 3617.011 |  |  | 1474.040 |  |  |
| TOTAL | 924.717 |  | 3617.011 |  |  | 1558.318 |  |  |
| Conc (wt %) |  |  |  |  | 15.53 |  | 5.35 |  |
| Flow Rate (ml/h) | 30.726 |  | 153.628 | 119.488 |  | 64.865 |  |  |
| Density (g/ml) | 1.254 |  | 0.981 |  | 1.040 |  | 1.001 |  |

The R fraction thus obtained is concentrated and atomized, giving a pinitol of 95% purity.

What is claimed is:

1. A method of obtaining pinitol from a pinitol-containing carob extract having the composition:

| Saccharose | 55–75% |
| --- | --- |
| Fructose | 7–15% |
| Glucose | 7–16% |
| Other sugars | 0.5–3% |
| Cyclitols | 4–14% |
| Organic and inorganic impurities | 0.5–2% | wherein the percentages are expressed in weight of dry matter, the method consisting of extracting carob to obtain said extract inverting the saccharose contained in the extract to fructose and glucose to obtain a syrup, subjecting the syrup to chromatographic separation of the pinitol from the sugars contained in the syrup, employing a strong cationic exchange resin to obtain a solution of pinitol in water containing 90% or greater pinitol content, based on dry weight, and recovering the separated pinitol.

2. The method as claimed in claim 1, wherein the chromatographic separation is a continuous moving-bed chromatographic separation using demineralized water as the only solvent.

3. The method as claimed in claim 2, wherein the chromatographic separation is carried out at between 10 to 70° C.

4. The method as claimed in claim 3, wherein the chromatographic separation is carried at about 60° C.

5. The method as claimed in claim 3, wherein the strong cationic exchange resin is salified.

6. The method as claimed in claim 5, wherein the strong cationic exchange resin is salified by sodium or calcium.

7. The method as claimed in claim 1, wherein the pinitol is recovered by concentration and contact with an organic solvent.

8. The method as claimed in claim 7, wherein the organic solvent is ethanol.

9. The method as claimed in claim 1, wherein the pinitol is recovered by atomization or freeze-drying.

* * * * *